United States Patent [19]
Losee et al.

[11] Patent Number: 6,149,211
[45] Date of Patent: *Nov. 21, 2000

[54] INCLUSION OF TOOTH WHITENING OXIDATION CHEMISTRIES INTO SLOW RELEASING FOOD PRODUCTS

[76] Inventors: Paul Losee, 2783 N. Hwy. 89, Layton, Utah 84041; F. Richard Austin, 2045 E. 2200 North, Layton, Utah 84090; Blaine D. Austin, 1811 N. Forest Ridge, Layton, Utah 84040

[*] Notice: This patent issued on a continued prosecution application filed under 37 CFR 1.53(d), and is subject to the twenty year patent term provisions of 35 U.S.C. 154(a)(2).

[21] Appl. No.: 09/028,330

[22] Filed: Feb. 24, 1998

Related U.S. Application Data

[63] Continuation-in-part of application No. 08/571,133, Dec. 12, 1995, abandoned.

[51] Int. Cl.[7] ................................. B65D 45/30
[52] U.S. Cl. .................. 292/258; 292/262; 292/258; 292/259; 292/288; 292/339
[58] Field of Search .................. 292/258, 262, 292/259, 288, 339

[56] References Cited

U.S. PATENT DOCUMENTS

| | | | |
|---|---|---|---|
| 3,574,825 | 4/1971 | Echeandia | 424/50 |
| 4,302,441 | 11/1981 | Muhlemann et al. | 424/48 |
| 4,522,805 | 6/1985 | Gordon | 424/52 |
| 4,587,119 | 5/1986 | Bucke et al. | 424/48 |
| 4,837,008 | 6/1989 | Rudy et al. | 424/53 |
| 4,897,258 | 1/1990 | Rudy et al. | 424/53 |
| 4,971,782 | 11/1990 | Rudy et al. | 424/53 |
| 4,988,500 | 1/1991 | Hunter et al. | 424/53 |
| 5,098,303 | 3/1992 | Fischer | 433/215 |
| 5,171,564 | 12/1992 | Nathoo et al. | 424/53 |
| 5,256,402 | 10/1993 | Prencipe et al. | 424/53 |
| 5,264,205 | 11/1993 | Kelly | 424/53 |
| 5,279,816 | 1/1994 | Church et al. | 424/53 |
| 5,302,375 | 4/1994 | Viscio | 424/53 |
| 5,314,701 | 5/1994 | Mentink et al. | 426/103 |
| 5,352,500 | 10/1994 | Mazurek et al. | 426/5 |
| 5,470,591 | 11/1995 | Ribadeau-Dumas et al. | 426/3 |
| 5,500,207 | 3/1996 | Goulet | 424/54 |
| 5,597,554 | 1/1997 | Wagner | 424/53 |
| 5,631,000 | 5/1997 | Pellico et al. | 424/53 |
| 5,709,895 | 1/1998 | Tanaka et al. | 426/96 |

*Primary Examiner*—Terressa Mosley
*Attorney, Agent, or Firm*—James L. Sonntag

[57] ABSTRACT

A solid tooth whitening composition in the form a table, gum, candy, or the like, is formed by combining carbamide peroxide with a non-hygroscopic sweetener base that comprises the hydrogenation product of isomaltulose. The composition may be stored for several weeks without detectable decomposition the carbamide peroxide to urea.

27 Claims, 2 Drawing Sheets

INCLUSION OF TOOTH WHITENING OXIDATION CHEMISTRIES INTO SLOW RELEASING FOOD PRODUCTS

RELATED APPLICATIONS

This application is a continuation-in-part of application Ser. No. 08/571,133, filed Dec. 12, 1995 now abandoned.

STATEMENT REGARDING FEDERALLY SPONSORED RESEARCH OR DEVELOPMENT (Not applicable)

FIELD OF THE INVENTION

This invention relates to a preparation for introduction of whitening chemicals to the surface of teeth and method of use and manufacture. More particularly, the present invention relates to such preparations in a solid, such as a candy, lozenge, gum, or tablet form, which is less costly and easier to use for the consumer than existing products available.

BACKGROUND OF THE INVENTION

The anatomy of a tooth is well known with an inner dentin layer and an outer hard surface enamel layer. Enamel is an opaque white or off-white color. It is the enamel that can become stained and/or discolored. The porous nature of the enamel layer allows stain and discoloring substances to enter the enamel surface and thereby discolor the tooth.

Many substances and food items, such as juices, tea, coffee and tobacco, can "stain" or reduce the "whiteness" of teeth. These substances are consumed on a daily basis and gradually over several months or years can impart a noticeable discoloration of the enamel surfaces of the teeth.

Presently the dental profession uses methods to whiten teeth that are based on the presentation of either hydrogen peroxide or carbamide peroxide in a gel preparation to the enamel surfaces of the teeth. These compounds come in varying strengths from 10 wt. % to 35 wt. %. The gels are delivered either by the dentist in the dental office, accompanied by light and/or heat, or by using home-use kits via plastic trays fitted to the teeth.

The home-use kits, which use low concentration compounds, require the fabrication of a plastic tray filled with a whitening gel before placement over the teeth. For proper fitting, a dentist must usually fabricate the tray. The treatment time is high and the activities of the consumer are restricted while the tray is in place. Generally several treatments are required. The disadvantage of this system is the lengthy time required to whiten teeth and the high inconvenience accompanying its use.

Faster whitening is accomplished by the dentist in the office, where the higher concentration gels are used. However, the cost to the consumer is higher and there is additional risk of the higher concentrations causing some soft tissue irritation. There is a demand in the marketplace for a less costly and more easily utilized whitening product which is without the constraints on time, the mess of the gels and lack of dental trays.

Candies, tablets, gums, and the like have been used as a vehicle for introducing various chemical agents to a tooth surface. A strict requirement, however, for these compositions is that they have a long shelf-life, at least on the order of several weeks. This requirement has limited the use of solids for tooth-whitening preparations, because in general the active components for tooth-whitening are not stable under ambient conditions of humidity and temperature. In solid compositions, these active components quickly become degraded to unsuitably low concentrations. In addition, the whitening compositions frequently degrade to reactions products with a bad taste. Thus, the compositions can become unpalatable even before the active component has degraded to insufficient levels.

An example of a tablet or gum or tooth treatment is disclosed in U.S. Pat. No. 4,302,441 issued to Muhlemann et al. on Nov. 24, 1981. This patent discloses a solid oral preparation comprising active urea hydrogen peroxide (carbamide peroxide) that is effective in countering acid fermentable carbohydrates in dental plaques. The solid oral composition in the form of a lozenge tablet or chewing gum comprises urea hydrogen peroxide and, in the absence of glycerol, and a sweetener selected from the group consisting of mannitol, sorbitol, xylitol and saccharin, and a carrier selected from the group consisting of soluble cellulose ethers and carbohydrate gums. These compositions may be effective in introducing carbamide peroxide to the surface of the teeth of the person to whom it is administered, but they suffer from having a short shelf life. In solid materials carbamide peroxide gradually reacts with ambient water such as from humidity in the air and with water in the composition to form urea and oxygen or hydrogen peroxide. This not only leads to a decrease in the effective amount of the carbamide peroxide, it also produces urea, which in small concentrations lends a sharp, unpleasant taste to the composition. Thus, even before the composition becomes ineffective from depletion of the carbamide peroxide it becomes unpalatable in only a few days and unacceptable as a consumer product.

Objects of the Invention

It is, therefore, an object of the invention to provide a system for delivering whitening agents to tooth surfaces that overcomes the shortcomings of the prior-art gel systems.

It is also an object of the invention to provide a whitening composition with a long shelf-life that does not degrade quickly to become unpalatable or ineffective.

An object of the invention is also to provide a system that is less costly and can be used by the consumer in a manner that does not restrict activity and requires an undue amount of time.

It is further an object of the invention to provide a composition in a solid form that is commercially acceptable, that is, introduces a sufficient carbamide peroxide to the tooth surface to provide a whitening effect, but also to provide sufficient stability that the product over a storage period of several weeks will not decompose to form urea to give the product an unpleasant taste.

It is further an object of the invention to provide a system that avoids the messy gels and liquids, and high peroxide concentrations.

Further objects of the invention will become evident in the description below.

BRIEF SUMMARY OF THE INVENTION

The present invention involves a composition and method for manufacture for a solid orally administered formulation. The active ingredient is carbamide peroxide. The formulation is water-free and comprises a non-hygroscopic sweetener, a hydrogenation product of isomaltulose, preferably the disaccharide, Isomalt. The formulation is stable, having a shelf life of several weeks. This contrasts with prior-art products that deteriorate quickly due to water in the composition or water adsorbed from the surrounding air. For the compositions of the invention, even after several weeks, there is no perceptible presence of bad tasting materials, particularly those that result from the reaction of carbamide peroxide with water.

The active ingredient in the present invention, carbamide peroxide, $CON_2H_4.H_2O_2$ is the addition compound of hydrogen peroxide and urea and is also known as urea peroxide, or urea hydrogen peroxide. The composition of the invention contains carbamide peroxide in a whitening effective amount, i.e., an amount to be efficacious to effect a whitening of teeth when taken orally and dissolved in the mouth or chewed to dissolve and release the carbamide peroxide. A efficacious amount has been found to be greater than about 3 wt. %. If the amount of carbamide peroxide is too high, greater than about 12 wt. %, it may impart an unpleasant taste to the composition. Suitable amounts for a commercially suitable product have been found to be between about 3.5 wt. % and about 10 wt. %.

As mentioned above, carbamide peroxide when reacted with water decomposes into urea. In the compositions of the present invention, the carbamide peroxide is isolated from water while in the product, so that it cannot react with water. This is accomplished by not adding any water during manufacture of the composition, and using materials that are as free from water as practical. In addition, the components of the composition are preferably non-hygroscopic and do not attract water from the atmosphere. In addition, the composition must have a physical and chemical nature that protects the carbamide peroxide from humidity in the air. It has been found, that composition with certain non-hygroscopic sweeteners, such as Mannitol, result in a unsatisfactory bad-tasting products. While not completely understood, it is believed that the unsatisfactory taste in these certain products may be due to an unsatisfactory taste of the sweetener itself, and/or from urea produced because the base material does not adequately isolate the carbamide peroxide from atmospheric moisture. Thus, the non-hygroscopic nature of the sweetener-base is the most important, but not the only factor. However, it has been found that when a hydrogenation product of isomaltulose is used as the sweetener base, the urea carbamide is stablized and protected and will not degrade over several weeks of storage.

The carbamide peroxide in the composition of the invention does not degrade and has a long shelf-life. But, as the product is orally administered and is dissolved by the saliva while being chewed or held in the mouth, it reacts with the saliva to produce a bleaching effect on the tooth surface without producing an unpleasant taste. It has been found that any urea that is formed in this process of dissolution in the mouth is insufficient to impart a bad taste to the product.

It has been found that prior-art gum, tablet and candy compositions contain water, or often contain substances that attract water from the humidity in the air. In normal gum, tablet and candy compositions, this water is no problem. But if carbamide peroxide is present, that water is available to react with and degrade the carbamide peroxide to urea, which is bad tasting even in very small concentrations.

In the method of the present invention, materials that are essentially free of water are used, or water is expelled from the composition. Because of the inherent properties of the base of the composition of the invention, there is no readsorbtion or attraction of water from the humidity in the air. Accordingly, the carbamide peroxide is protected or shielded from water and the decomposition reaction does not take place sufficiently to produce an unpleasant taste. Accordingly, it has been found that the compositions of the present invention can be stored for several weeks with no detectable deterioration in taste and with an insignificant loss of the active ingredient.

The compositions of the invention consists essentially of the active ingredient, urea carbamide, and a base or sweetener composition. For purposes of this disclosure the base composition is the portion of the composition of the invention other than the carbamide peroxide component. The major portion (>50 wt. %) of base composition comprises a hydrogenation product of isomaltulose as the sole or principal sweetener. The base also comprises other materials used conventionally to form the appropriate gum, tablet or candy. The base is essentially water-free and non-hygroscopic. By "water-free" is meant that it contains negligible water that is free to react with the carbamide peroxide. Components of the composition may contain waters of hydration, but they must be bound sufficiently to the base composition or present in such a small amount to provide negligible reactive water.

By "non-hygroscopic" is meant a composition lacking a hygroscopic property, i.e., the tendency of the substance to hydrate by absorbing water, usually from the ambient humidity. The base material should be non-hygroscopic at ambient temperatures and humidities usually encountered during handling and storage. The composition of the invention may comprise materials that are hygroscopic, but they must be present in small enough amounts, such that the essentially non-hygroscopic nature of the entire base composition is retained.

The sole or major sweetener of the base composition is a catalytically hydrogenation product of isomaltulose (6-0-α-D-Glucopyranosyl-D-fructose). The catalytic hydrogenation of isomaltulose (a derivative of sucrose) produces two stereo isomers, 6-0-α-D-Glucopyranosyl-D-sorbitol (1,6-GPS) and 1-0-α-D-Glucopyranosyl-D-mannitol (1,1-GPM). (These are also known as "-D-glucopyranosyl-1,6-D-sorbitol and "-D-glucopyranosyl-1,1-D-mannitol, respectively.) The hydrogenation reaction is illustrated below.

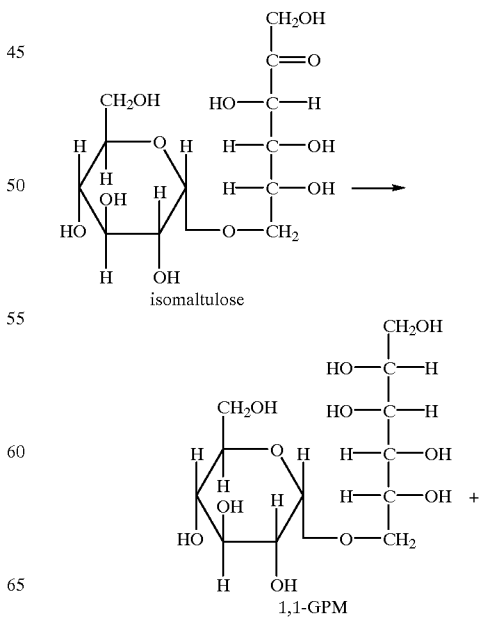

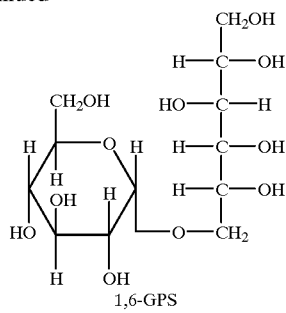

1,6-GPS

Isomalt is an equimolar mixture of the two isomeric disaccharide polyols, 1,6-GPS and 1,1-GPM. Isomalt is sold under the trademark Palatinit™ by Palatinit Süssungsmittel GmbH, Mannheim, Germany. Isomalt is non-hygroscopic, particularly at ambient temperatures and humidities. At 25° C., Isomalt absorbs very little water. At temperatures as high as 60° C. and 80° C. the relative humidity must be 75% and 65% respectively for significant water absorption. A detailed discussion of Isomalt, its manufacture and various properties is disclosed in Isomalt, by Peter Sträter and William E. Irwin in Alternative Sweeteners, edited by Lyn O'Brien Nabors and Robert C. Gellardi, Marcel Dekker, Inc., 1992, and ISOMALT, 5th edition, published in 1996 by Platinit Süssungsmittel GmbH, Gottlieb-Daimler-Straβe, D-68165, Mannheim, Germany. The hydrogenation reaction of isomaltulose is disclosed in U.S. Pat. No. 4,117,173 to Schiweck et al.

The base composition may comprise other suitable ingredients that are used in candy and tablet compositions, such as other non-hygroscopic sweeteners, flavors, sweeteners, anti-oxidants, stabilizers, colorants, and the like.

The composition of the invention is made by any suitable process where carbamide peroxide is incorporated into the solid base material such that the carbamide peroxide is protected or shielded from humidity in the atmosphere, and no water or no hygroscopic materials that would absorb water are introduced that would result in water being introduced into the composition during processing or storage in an amount that would produce a taste-detectable amount of urea over several days or weeks.

One method for manufacturing the composition of the invention comprises first heating the base material to a temperature sufficient to drive off any water in the composition. For Isomalt, this is a temperature of about 150° C. or above. The base material is then cooled to a temperature at which the carbamide peroxide can be incorporated and mixed into the base material. As the temperature approaches near is 120° C., the carbamide peroxide disassociates. Accordingly, the preferred mixing temperature is 118° C. or below. When Isomalt cools to near 110° C. it becomes difficult to mix the carbamide peroxide in an Isomalt base. Accordingly the preferred temperature for mixing in Isomalt is 114° C. or above. In summary, for mixing carbamide peroxide in Isomalt, the mixing temperature is preferably between 114° C. and 118° C., more preferably about 116° C.

After incorporating the carbamide peroxide, the material is then allowed to solidify. The solid base can be formed into hard candy shapes by any suitable method, or crushed into powder and then hard pressed in to tablets, or otherwise processed by conventional methods into a solid form that can be orally administered. Basically, any process that permits the heating to expel the water and the mixing temperature of the carbamide peroxide is suitable for the present invention. The other components of the composition, i.e., the sweeteners, stabilizers, flavors, etc. are added at any suitable time, as dictated by their properties.

Alternately, a composition of the invention may be produced by compressing into the tablets a powdered base material (as defined above) and a powdered carbamide peroxide.

When the composition of the invention is placed within the mouth and is allowed to dissolve or is chewed, the composition slowly dissolves adjacent to the teeth which provides an effective amount of the carbamide peroxide to the surface of the tooth. Preferably, a gum, candy or tablet of the invention is formed so as to dissolve the carbamide peroxide slowly over about a 20 minute period. A consistent daily use of the tablets of the invention will then obtain a maximum whitening of the teeth of the consumer.

DETAILED DESCRIPTION OF THE INVENTION

Figure 1:
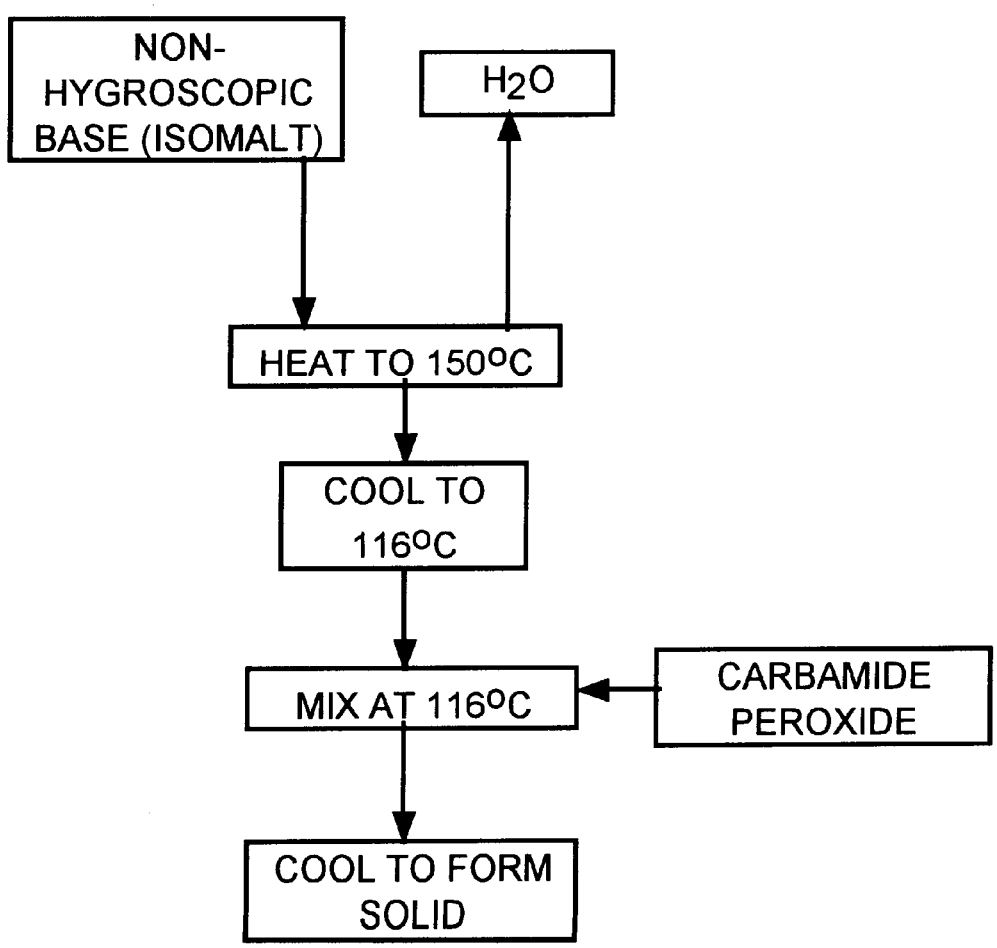
FIG. 1 is a flow diagram of a process of the invention.

Referring to FIG. 1, which is a flow sheet of a method for manufacture of the composition of the invention, a non-hygroscopic base, as defined herein, is provided and heated to 150° C. to drive of the water in the base. The base is cooled to 116° C., the temperature at which carbamide peroxide is added and mixed. The material is then allowed to cool to form a solid material.

Figure 2:
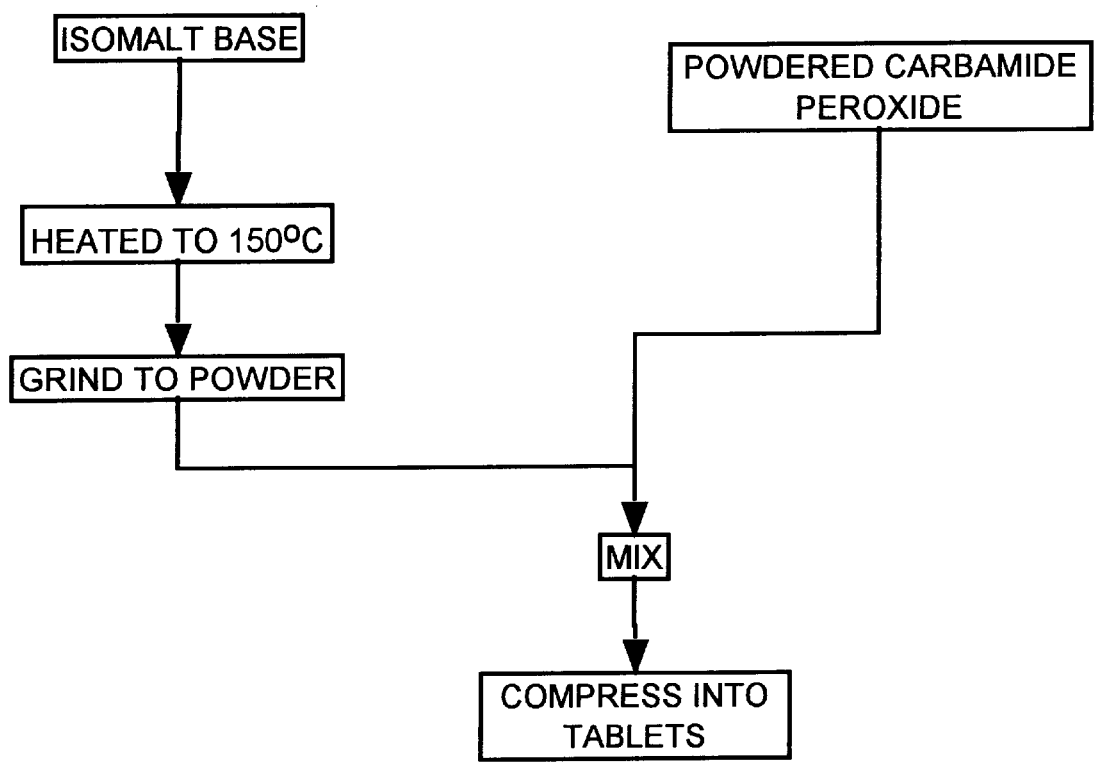
FIG. 2 is a flow diagram of another process of the invention.

FIG. 2 is a flow sheet of an alternate method for manufacture of the composition of the invention. A non-hygroscopic base is provided optionally heated to 150° C. to drive off moisture. The base is then ground and mixed with powdered carbamide peroxide and the mixture is compressed into tablets by conventional techniques.

EXAMPLES

Example I

Hard Candy Composition

Candy bases were made and formed into hard candies according to the invention.

A base mixture comprising Isomalt and the ingredients shown in Table A were compounded by conventional candy making technique and then heated to a temperature of 150° C. for a sufficient period to drive of any free water. The mixture was then cooled to 116° C. and the active ingredient, carbamide peroxide, was added. The other ingredients were added and compounded according to standard candy making practice. The composition was then allowed to cool and was molded formed into candy shapes by conventional techniques. Alternately, the composition is allowed to solidify, ground, and the ground composition pressed into tablets. The amounts of the ingredients in percent, based upon the original unheated mixture and the final product are shown in Table A.

TABLE A

CANDY FORMULATION

| | Mixture (wt. %) | Final Composition (wt. %) |
|---|---|---|
| Base Ingredients | | |
| Isomalt | 78.0 | 93.19 |
| Titanium Dioxide | 0.2 | 0.24 |
| Aspartame | 0.85 | 1.0 |
| Deionized Water | 16.30 | |
| Flavoring (Pina Cola) | 0.65 | 0.78 |
| Active Ingredient | | |
| Carbamide Peroxide | 4.0 | 4.78 |

Example II

A candy composition was made, essentially as in Example I, except a different flavor was used. The amounts of the ingredients as a percentage of the initial mix are shown in Table B.

TABLE B

CANDY FORMULATION

| | Mix (wt. %) |
|---|---|
| Base Ingredient | |
| Isomalt | 78.0 |
| Titanium Dioxide | 0.2 |
| Aspartame | 0.85 |
| Flavoring (Spearmint) | 0.40 |
| Water | 16.55 |
| Active Ingredient | |
| Carbamide Peroxide | 4.0 |

Example III

A hard candy composition was made essentially as in Example I except that Vitamin E was added as an antioxidant and a preservative. The amounts of the ingredients as a percentage of the initial mix and the composition of the final product are shown in Table C.

TABLE C

VITAMIN E CANDY FORMULATION

| | Mix (wt. %) | Final Composition (wt. %) |
|---|---|---|
| Base Ingredient | | |
| Isomalt | 78.2 | 90.20 |
| Titanium Dioxide | 0.2 | 0.23 |
| Aspartame | 0.85 | 0.98 |
| Water | 13.30 | — |
| Flavoring (Cherry) | 0.65 | 0.75 |
| Vitamin E | 3.0 | 3.46 |
| Active Ingredient | | |
| Carbamide Peroxide | 3.8 | 4.38 |

Example IV

A composition was produced in the form of a tablet. This was accomplished by mixing essentially water-free Isomalt in the powder form with the other ingredients in powder form, and pressing the powder mixture into tablets by conventional techniques. Isomalt is available commercially in an essentially water-free condition. Alternately, the Isomalt may be heated to 150° C. (to expel water), resolidified and ground to form a power. The composition of a tablet in grams and wt. % of the ingredients are shown in Table D.

TABLE D

TABLET COMPOSITION 10% ACTIVE INGREDIENT

| | Grams | (wt. %) |
|---|---|---|
| Base Ingredient | | |
| Isomalt | 50 | 79.66 |
| Citric Acid | 0.2 | 0.32 |
| Vanilla | 3.5 | 5.58 |
| NutraSweet | 0.95 | 1.51 |
| Magnesium Stearate | 1.5 | 2.39 |
| Peppermint Oil | 0.32 | 0.51 |
| Active Ingredient | | |
| Carbamide Peroxide | 6.3 | 10.04 |
| TOTAL | 62.77 | 100.00 |

COMPARATIVE EXAMPLES

Comparative Example I

Compositions were made, essentially as described in Example I, except that alternate sweeteners in base were substituted for the Isomalt. The final products were stored in ambient room-temperature/humidity conditions and periodically tested for taste and amount of active ingredient (AI) remaining in the composition. The base materials used were mannitol, sorbitol, and xylitol. In compositions with these materials there was a noticeable urea taste after 2 days. The amount of the carbamide peroxide active ingredient decreased from 4 wt. % to 2 wt. % in 6 days. Basically, for all the comparative compositions made from hygroscopic bases, the composition became unefficacious and unpalatable in less than one week due to the decomposition of the carbamide peroxide.

As a comparison, composition made according to Examples I to IV above were made and stored under similar conditions. After one month there was no detectable change in taste and no detectable decrease in the amount of carbamide peroxide.

Comparative Example II

Compositions of the invention and comparative compositions were made as tablets. The compositions of the invention were made using Isomalt as the sweetener for the base, essentially as in Example IV. Comparative compositions were made by substituting other sweeteners for the Isomalt. The other sweeteners used were mixtures of Sorbitol, Xylitol, and Mannitol, as shown in Table E.

The compositions were tested by measuring the amount of carbamide peroxide to determine the loss of the active ingredient. Each composition was also tasted and rated for a palatable, satisfactory taste (P) or a non-palatable, non-satisfactory taste (NP) after being stored for a period of time, as indicated in Table E. The results are summarized in Table E.

TABLE E

| | Carbamide Peroxide Degradation | | | |
|---|---|---|---|---|
| | | wt. % Carbamide Peroxide lost | | |
| | Taste in 48 hrs. | 48 hr. | 2 weeks | 4 weeks |
| Isomalt | P | 0 | 0 | 0 |
| Sorbitol/Xylitol | NP | 2 | 10 | >15 |
| Sorbitol/Mannitol | NP | 2 | 10 | >17 |
| Mannitol/Xylitol | NP | 1 | 8 | >15 |

Comparative Example III

A composition of the invention and comparative compositions were and tested as in Comparative Example III. The tests and results are summarized in Table F.

TABLE F

| | Carbamide Peroxide Degradation | | | | |
|---|---|---|---|---|---|
| | Taste | | wt. % Carbamide Peroxide lost | | |
| | 48 hrs. | 6 weeks | 1 week | 2 weeks | 4 weeks |
| Isomalt | P | P | 0 | 0 | 0 |
| Sorbitol | NP | NP | 10 | 17 | 35 |
| Sorbitol/Xylitol | NP | NP | 10 | 17 | 35 |
| Sorbitol/Mannitol | NP | NP | 9 | 18 | 40 |
| Mannitol/Xylitol | NP | NP | 9 | 18 | 9 |
| Mannitol | NP | NP | — | — | — |

As seen from the above comparative examples, only the compositions of the invention, those using Isomalt could be stored satisfactorily. The comparative examples quickly developed an unsatisfactory taste, believed to be due to the presence of urea. As shown in Table E, even a 1 wt. % loss of carbamide peroxide to urea production resulted in a unsatisfactory taste.

The compositions of the invention had no detectable amounts of urea, and their taste was satisfactory, even after several weeks, which indicated that urea was not present, even in the small amounts that can be detected by taste.

As seen from the above data, the use of the non-hygroscopic base material, the hydrogenation product of isomaltulose, is critical to the invention. The candy compositions with the alternate sweeteners in the base materials all exhibited poor shelf life. In comparison, the composition of the invention shows excellent shelf life with no urea taste nor significant deterioration of the carbamide peroxide.

While this invention has been described with reference to certain specific embodiments and examples, it will be recognized by those skilled in the art that many variations are possible without departing from the scope and spirit of this invention, and that the invention, as described by the claims, is intended to cover all changes and modifications of the invention which do not depart from the spirit of the invention.

What is claimed is:

1. A solid composition for whitening teeth consisting essentially of;
    carbamide peroxide in an amount effective to dissolve and produce a whitening effect on teeth when the composition is dissolved in the mouth,
    a non-hygroscopic solid base comprising a hydrogenation product of isomaltulose as a major component of the base and as the main or sole sweetener.

2. A solid composition for whitening of teeth as in claim 1 wherein the sweetener comprises 6-0-α-D-Glucopyranosyl-D-sorbitol.

3. A solid composition for whitening of teeth as in claim 1 wherein the sweetener comprises 1-0-α-D-Glucopyranosyl-D-mannitol.

4. A solid composition for whitening of teeth as in claim 1 wherein the sweetener comprises a mixture of 6-0-α-D-Glucopyranosyl-D-sorbitol and 1-0-α-D-Glucopyranosyl-D-mannitol.

5. A solid composition for whitening of teeth as in claim 1 wherein the sweetener comprises an isometric mixture of 6-0-α-D-Glucopyranosyl-D-sorbitol and 1-0-α-D-Glucopyranosyl-D-mannitol.

6. A solid composition for whitening of teeth as in claim 1 wherein the carbamide peroxide is present in the composition in an amount above about 3 weight percent and below 12 weight percent.

7. A solid composition for whitening of teeth as in claim 1 wherein the carbamide peroxide is present in the composition in an amount above about 3.5 weight percent and below 10 weight percent.

8. A solid composition for whitening of teeth as in claim 1 wherein the composition is in the form of a tablet.

9. A solid composition for whitening of teeth as in claim 1 wherein the composition is in the form of a candy.

10. A solid composition for whitening of teeth as in claim 1 wherein the composition is in the form of a gum.

11. A non-hygroscopic solid tooth whitening composition comprising;
    carbamide peroxide in an amount effective to dissolve and produce a whitening effect on teeth when the composition is dissolved in the mouth,
    a solid, water-free, non-hygroscopic base comprising a hydrogenation product of isomaltulose,
with water in the composition at sufficiently low amount and the composition being sufficiently non-hygroscopic to avoid a detectable taste of urea from the reaction of carbamide peroxide with water.

12. A non-hygroscopic solid tooth whitening composition as in claim 11 wherein the sweetener comprises 6-0-α-D-Glucopyranosyl-D-sorbitol.

13. A non-hygroscopic solid tooth whitening composition as in claim 11 wherein the sweetener comprises 1-0-α-D-Glucopyranosyl-D-mannitol.

14. A non-hygroscopic solid tooth whitening composition as in claim 11 wherein the sweetener comprises a mixture of 6-0-α-D-Glucopyranosyl-D-sorbitol and 1-0-α-D-Glucopyranosyl-D-mannitol.

15. A non-hygroscopic solid tooth whitening composition as in claim 11 wherein the sweetener comprises an isometric mixture of 6-0-α-D-Glucopyranosyl-D-sorbitol and 1-0-α-D-Glucopyranosyl-D-mannitol.

16. A non-hygroscopic solid tooth whitening composition as in claim 11 wherein the carbamide peroxide is present in the composition in an amount above about 3 weight percent and below 12 weight percent.

17. A non-hygroscopic solid tooth whitening composition as in claim 11 wherein the carbamide peroxide is present in the composition in an amount above about 3.5 weight percent and below 10 weight percent.

18. A non-hygroscopic solid tooth whitening composition as in claim 11 wherein the composition is in the form of a tablet.

19. A non-hygroscopic solid tooth whitening composition as in claim 11 wherein the composition is in the form of a candy.

20. A non-hygroscopic solid tooth whitening composition as in claim 11 wherein the composition is in the form of a gum.

21. A method for manufacturing a solid tooth whitening composition comprising compounding into a mixture a tooth-whitening amount of carbamide peroxide and a non-hygroscopic base of a hydrogenation product of isomaltulose in a water-free environment, forming the mixture into a solid shape.

22. A method for manufacturing a solid tooth whitening composition as in claim 21 wherein the carbamide peroxide and the non-hygroscopic base are compounded as powders, and the solid shape is chosen from the group consisting of tablets, gums, and candies.

23. A method of manufacturing a solid tooth-whitening composition comprising;

providing an essentially non-hygroscopic base sweetener base comprising the hydrogenation product of isomaltulose, melting the base to a temperature sufficient to drive essentially all of the free water from the base, mixing a tooth whitening amount of carbamide peroxide into the melted base at a temperature below the decomposition temperature of carbamide peroxide, allowing to cool to form a solid composition of the sweetener base and the carbamide peroxide.

24. A method for manufacturing a solid tooth whitening composition comprising;

compounding an essentially water-free, non-hygroscopic base and a tooth-whitening amount of carbamide peroxide, the water-free, non-hygroscopic base comprising a hydrogenation product of isomaltulose, with water in the composition at sufficiently low amount and the composition being sufficiently non-hygroscopic to avoid a detectable taste of urea from the reaction of carbamide peroxide with water, forming the base and carbamide peroxide into a solid shape.

25. A method of whitening teeth comprising;

dissolving in the mouth a solid composition consisting essentially of;

carbamide peroxide in an amount effective to dissolve and produce a whitening effect on teeth when the composition is dissolved in the mouth, a non-hygroscopic solid base comprising a sweetener which is a hydrogenation product of isomaltulose.

26. A method of whitening teeth comprising;

dissolving in the mouth a solid composition comprising carbamide peroxide in an amount effective to produce a whitening effect on teeth when the composition is dissolved in the mouth, and a solid, essentially water-free, non-hygroscopic base, the solid, water-free, non-hygroscopic base comprising a hydrogenation product of isomaltulose, with water in the composition at sufficiently low amount and the composition being sufficiently non-hygroscopic to avoid a detectable taste of urea from the reaction of carbamide peroxide with water.

27. A method for stabilizing carbamide peroxide in a solid material;

compounding the carbamide peroxide with an essentially water-free, non-hygroscopic sweetener base to form the solid material, the water-free, non-hygroscopic base comprising a hydrogenation product of isomaltulose, with water in the composition at sufficiently low amount and the composition being sufficiently non-hygroscopic to avoid a detectable taste of urea from the reaction of carbamide peroxide with water.

* * * * *